(12) United States Patent
Kennan et al.

(10) Patent No.: US 8,586,669 B2
(45) Date of Patent: Nov. 19, 2013

(54) SILICONE PASTE COMPOSITIONS

(75) Inventors: John Joseph Kennan, Nonthaburi (TH);
Kathryn Elizabeth Messner, Midland, MI (US); Isabelle Van Reeth, Shanghai (CN); Robert O. Huber, Midland, MI (US); Gerald K. Schalau, II, Freeland, MI (US); Concettina Scavuzzo, Lez-Herlaimont (BE)

(73) Assignee: Dow Corning Corporation, Midland, MI (US)

( * ) Notice: Subject to any disclaimer, the term of this patent is extended or adjusted under 35 U.S.C. 154(b) by 140 days.

(21) Appl. No.: 13/142,899

(22) PCT Filed: Jan. 5, 2010

(86) PCT No.: PCT/US2010/020110
§ 371 (c)(1),
(2), (4) Date: Jun. 30, 2011

(87) PCT Pub. No.: WO2010/080755
PCT Pub. Date: Jul. 15, 2010

(65) Prior Publication Data
US 2011/0268677 A1 Nov. 3, 2011

Related U.S. Application Data

(60) Provisional application No. 61/142,984, filed on Jan. 7, 2009.

(51) Int. Cl.
*A61K 8/02* (2006.01)

(52) U.S. Cl.
USPC .............................. 524/588; 424/59; 424/401

(58) Field of Classification Search
USPC ..................................... 524/588; 424/59, 401
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,296,291 A | 1/1967 | Chalk | |
| 3,419,593 A | 12/1968 | Willing | |
| 3,516,946 A | 6/1970 | Modic | |
| 3,814,730 A | 6/1974 | Karstedt | |
| 3,928,629 A | 12/1975 | Chandra et al. | |
| 3,989,668 A | 11/1976 | Lee et al. | |
| 4,985,459 A | 1/1991 | Sunshine et al. | |
| 5,036,117 A | 7/1991 | Chung et al. | |
| 5,175,325 A | 12/1992 | Brown et al. | |
| 5,412,004 A * | 5/1995 | Tachibana et al. | 524/27 |
| 5,760,116 A | 6/1998 | Kilgour et al. | |
| 5,880,210 A | 3/1999 | Schulz, Jr. et al. | |
| 5,889,108 A | 3/1999 | Zhang | |
| 6,605,734 B2 | 8/2003 | Roy et al. | |
| 6,987,157 B2 | 1/2006 | Clement et al. | |
| 2002/0037974 A1 | 3/2002 | Kilgour et al. | |

FOREIGN PATENT DOCUMENTS

| | | |
|---|---|---|
| EP | 0501791 | 11/1996 |
| EP | 1148099 | 10/2001 |
| WO | 2007109240 | 9/2007 |
| WO | 2009006091 | 1/2009 |

* cited by examiner

*Primary Examiner* — Margaret Moore
(74) *Attorney, Agent, or Firm* — Alan Zombeck

(57) ABSTRACT

Silicone paste compositions are disclosed by combining a silicone organic elastomer gel with water or a hydrophilic solvent. The silicone paste compositions may further contain a personal or healthcare active. The silicone organic elastomer gel is prepared by reacting in a carrier fluid an organohydrogensiloxane with two polyoxyalkylenes, the first polyoxyalkylene having aliphatic unsaturation at both each molecular termini, and the second polyoxyalkylene having aliphatic unsaturation at one molecular terminal.

16 Claims, 3 Drawing Sheets

SILICONE PASTE COMPOSITIONS

CROSS REFERENCE TO RELATED APPLICATIONS

This application is a U.S. national stage filing under 35 U.S.C. §371 of PCT Application No. PCT/US10/20110 filed on 5 Jan. 2010, currently pending, which claims the benefit of U.S. Provisional Patent Application No. 61/142,984 filed 7 Jan. 2009 under 35 U.S.C. §119(e). PCT Application No. PCT/US10/20110 and U.S. Provisional Patent Application No. 61/142,984 are hereby incorporated by reference.

TECHNICAL FIELD

This disclosure relates to silicone paste compositions by combining a silicone organic elastomer gel with water or a hydrophilic solvent. The silicone paste compositions may further contain a personal or healthcare active. The silicone organic elastomer gel is prepared by reacting in a carrier fluid an organohydrogensiloxane with two polyoxyalkylenes, the first polyoxyalkylene having aliphatic unsaturation at both each molecular termini, and the second polyoxyalkylene having aliphatic unsaturation at one molecular terminal.

BACKGROUND

Silicone elastomer gels and pastes impart desirable properties to a variety of formulations. They can be used as rheology modifiers or thickeners. In personal care formulations, they are often valued for imparting desirable aesthetics such as skin feel to a formulation. They may also be used to deliver actives to a surface. Silicone elastomer gels are typically prepared by crosslinking organopolysiloxanes to form a silicone elastomer in the presence of a swelling solvent. During and/or after the crosslinking step, the swollen silicone elastomer is sheared to create a paste. The paste can be subject to additional processing such as the addition of more solvent, inhibitors, or active ingredients and subject to additional shear to give a uniform paste. Silicone elastomers are most commonly dispersed in a volatile silicone carrier fluid to form gelled compositions. Representative examples of such silicone elastomers are taught in U.S. Pat. No. 5,880,210, and U.S. Pat. No. 5,760,116.

PCT/US2008/67989 discloses silicone elastomer gels having greater compatibility with organic carrier fluids and organic actives of interest in personal care by crosslinking the silicone elastomer with a hydrophobic polyalkylene oxide.

While PCT/US2008/67989 provides silicone elastomer gels having greater compatibility with organic carrier fluids and actives, there is still a further need to incorporate aqueous or hydrophilic ingredients with these silicone elastomeric gels while reducing or eliminating the need to use additional surfactants or emulsifiers. Addition of surfactants and emulsifiers can limit formulation latitude and decrease aesthetics. Thus, there is a need to identify such compatibilized compositions that are stable when formulated as a personal or healthcare product. Furthermore, there is a need identify such composition having the aesthetic qualities associated with silicone elastomer gels.

SUMMARY

The present inventors have discovered certain silicone paste compositions that are able to compatibilize organic fluids and actives with aqueous or hydrophilic based substances. The silicone pastes are obtained from a silicone organic elastomer gel containing polyoxyalkylene crosslinked silicone elastomers also having pendant polyoxyalkylene groups, the selection and amount of polyoxyalkene groups that are incorporated into the silicone elastomer is such so as to provide the silicone elastomer with 2 to 25 weight percent ethylene oxide groups. The present paste compositions are able to incorporate aqueous and hydrophilic substances with a variety of personal and healthcare actives. The present paste compositions have rheological properties that provide desirable aesthetics when applied as a skin care formulation.

DETAILED DESCRIPTION

Figure 1:
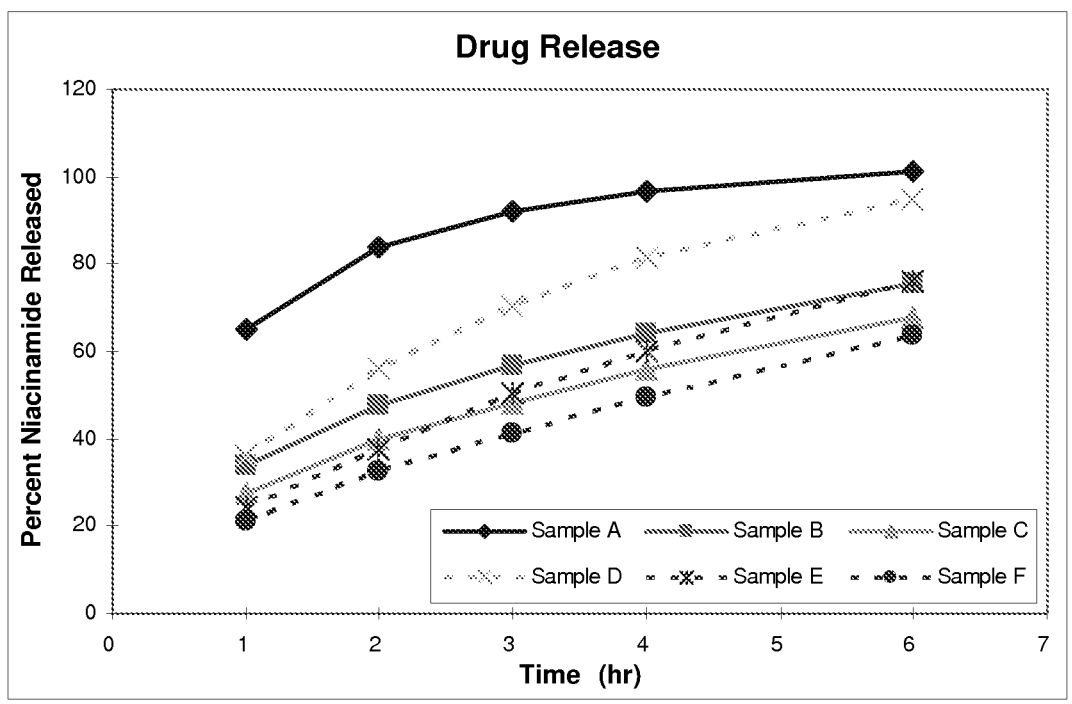
FIGS. 1 to 3 show release data of the active ingredient versus time, as explained in more detail in Examples 5 to 7.

The present paste compositions contain a) a silicone organic elastomer gel and b) water or a hydrophilic solvent. The silicone organic elastomer gel contains i) a silicone organic elastomer and ii) a hydrophobic carrier fluid. The amounts of the silicone organic elastomer and hydrophobic carrier fluid used in the silicone organic elastomer gel may vary from 2 to 95 weight % of the silicone organic elastomer and 5 to 98 weight % of a hydrophobic carrier fluid, providing the sum of each is 100 weight percent. Additional components besides i) and ii) may be added to the silicone organic elastomer gel, in which case the amounts of all components used should sum to 100 weight percent.

The silicone organic elastomer used in the present gel is obtained by reacting;

A) an organohydrogensiloxane comprising siloxy units of average

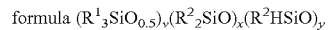

formula $(R^1{}_3SiO_{0.5})_v(R^2{}_2SiO)_x(R^2HSiO)_y$, wherein $R^1$ is hydrogen or $R^2$,
$R^2$ is a monovalent hydrocarbyl,
$v \geq 2$, $x \geq 0$, $y \geq 2$, B) a first polyoxyalkylene having the average formula

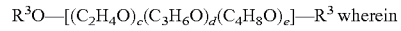

$R^3O-[(C_2H_4O)_c(C_3H_6O)_d(C_4H_8O)_e]-R^3$ wherein $R^3$ is a monovalent unsaturated aliphatic hydrocarbon group containing 2 to 12 carbon atoms,
c is from 0 to 50, d is from 0 to 100, e is from 0 to 100, with a proviso the ratio of (d+e)/(c+d+e) is greater than 0.5, C) a hydrosilylation catalyst, D) a second polyoxyalkylene having the average formula

$R^3O-[(C_2H_4O)_{c'}(C_3H_6O)_{d'}(C_4H_8O)_e]-R^4$ where $R^3$ is a monovalent unsaturated aliphatic hydrocarbon group containing 2 to 12 carbon atoms,
c' is greater than 4, d' and e may vary from 0 to 100,
$R^4$ is hydrogen, an acyl group, or a monovalent hydrocarbon group containing 1 to 8 carbons, in the presence of a hydrophobic carrier fluid.

A) The Organohydrogensiloxane

Component A) is a linear or branched organohydrogensiloxane having have the average formula $(R^1{}_3SiO_{0.5})_v$ $(R^2{}_2SiO)_x(R^2HSiO)_y$, wherein $R^1$ is hydrogen or $R^2$,
$R^2$ is a monovalent hydrocarbyl,
$v \geq 2$,
$x \geq 0$, alternatively x=1 to 500, alternatively x=1 to 200,
$y \geq 2$, alternatively y=2 to 200, alternatively y=2 to 100.

$R^2$ may be a substituted or unsubstituted aliphatic or aromatic hydrocarbyl. Monovalent unsubstituted aliphatic hydrocarbyls are exemplified by, but not limited to alkyl groups such as methyl, ethyl, propyl, pentyl, octyl, undecyl, and octadecyl and cycloalkyl groups such as cyclohexyl. Monovalent substituted aliphatic hydrocarbyls are exemplified by, but not limited to halogenated alkyl groups such as chloromethyl, 3-chloropropyl, and 3,3,3-trifluoropropyl. The aromatic hydrocarbon group is exemplified by, but not limited to, phenyl, tolyl, xylyl, benzyl, styryl, and 2-phenylethyl.

In one embodiment, the organohydrogensiloxane may contain additional siloxy units and have the average formula

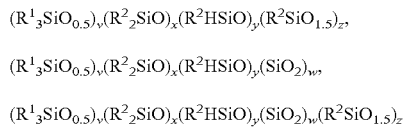

$(R^1{}_3SiO_{0.5})_v(R^2{}_2SiO)_x(R^2HSiO)_y(R^2SiO_{1.5})_z$, $(R^1{}_3SiO_{0.5})_v(R^2{}_2SiO)_x(R^2HSiO)_y(SiO_2)_w$, $(R^1{}_3SiO_{0.5})_v(R^2{}_2SiO)_x(R^2HSiO)_y(SiO_2)_w(R^2SiO_{1.5})_z$ or any mixture thereof,
where
$R^1$ is hydrogen or $R^2$,
$R^2$ is a monovalent hydrocarbyl,
and $v \geq 2$, $w \geq 0$, $x \geq 0$, $y \geq 2$, and $z$ is $\geq 0$.

In one embodiment, the organohydrogensiloxane is selected from a dimethyl, methyl-hydrogen polysiloxane having the average formula;

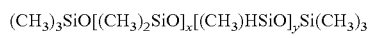

$(CH_3)_3SiO[(CH_3)_2SiO]_x[(CH_3)HSiO]_ySi(CH_3)_3$ where $x \geq 0$, alternatively, x=1 to 500, alternatively x=1 to 200, and $y \geq 2$, alternatively, y=2 to 200, alternatively y=2 to 100.

Methods for preparing organohydrogensiloxanes are well known, and many are sold commercially.

B) The First Polyoxyalkylene

Component B) is a polyoxyalkylene having an average formula

$R^3O\text{---}[(C_2H_4O)_c(C_3H_6O)_d(C_4H_8O)_e]\text{---}R^3$ wherein
$R^3$ is a monovalent unsaturated aliphatic hydrocarbon group containing 2 to 12 carbon atoms,
c is from 0 to 50, alternatively 0 to 10, or alternatively less than 2,
d is from 0 to 100, alternatively 1 to 100, or alternatively 5 to 50,
e is from 0 to 100, alternatively 0 to 50, or alternatively 0 to 30, with a proviso the ratio of (d+e)/(c+d+e) is greater than 0.5, alternatively greater than 0.8, or alternatively greater than 0.95.

The polyoxyalkylene useful as component B) is a polyoxyalkylene that is terminated at each molecular chain end (i.e. alpha and omega positions) with a unsaturated aliphatic hydrocarbon group containing 2 to 12 carbon atoms. The polyoxyalkylene may result from the polymerization of ethylene oxide, propylene oxide, butylene oxide, 1,2-epoxyhexane, 1,2-epoxyoctance, cyclic epoxides such as cyclohexene oxide or exo-2,3-epoxynorborane. The polyoxyalkylene group may comprise oxyethylene units ($C_2H_4O$), oxypropylene units ($C_3H_6O$), oxybutylene units ($C_4H_8O$), or mixtures thereof. Typically, the polyoxyalkylene group comprises a majority of oxypropylene or oxybutylene units, as defined on a molar basis and indicated in the above formula by the c, d, and e subscripts. The unsaturated aliphatic hydrocarbon group can be an alkenyl or alkynyl group. Representative, non-limiting examples of the alkenyl groups are shown by the following structures; $H_2C{=}CH\text{---}$, $H_2C{=}CH\;CH_2\text{---}$, $H_2C{=}C(CH_3)CH_2\text{---}$, $H_2C{=}CHCH_2CH_2\text{---}$, $H_2C{=}CH\;CH_2CH_2CH_2\text{---}$, and $H_2C{=}CHCH_2CH_2CH_2CH_2\text{---}$. Representative, non-limiting examples of alkynyl groups are shown by the following structures; $HC{\equiv}C\text{---}$, $HC{\equiv}CCH_2\text{---}$, $HC{\equiv}CC(CH_3)\text{---}$, $HC{\equiv}CC(CH_3)_2\text{---}$, $HC{\equiv}CC(CH_3)_2CH_2\text{---}$.

In one embodiment, the polyoxyalkylene is selected from
$H_2C{=}CHCH_2O[C_3H_6O]_dCH_2CH{=}CH_2$,
$H_2C{=}C(CH_3)CH_2O[C_3H_6O]_dCH_2C(CH_3){=}CH_2$,
$HC{\equiv}CCH_2O[C_3H_6O]_dCH_2C{\equiv}CH$, or
$HC{\equiv}CC(CH_3)_2O[C_3H_6O]_dC(CH_3)_2C{\equiv}CH$
where d is as defined above.

Polyoxyalkylenes having an unsaturated aliphatic hydrocarbon group at each molecular terminal are known in the art, and many are commercially available. Polyoxyalkylenes having an unsaturated aliphatic hydrocarbon group at each molecular terminal are commercially available from NOF (Nippon Oil and Fat, Tokyo, Japan) and Clariant Corp. (Charlottesville, N.C.).

(C) The Hydrosilylation Catalyst

Component (C) comprises any catalyst typically employed for hydrosilylation reactions. It is preferred to use platinum group metal-containing catalysts. By platinum group it is meant ruthenium, rhodium, palladium, osmium, iridium and platinum and complexes thereof. Platinum group metal-containing catalysts useful in preparing the compositions of the present invention are the platinum complexes prepared as described by Willing, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation. The platinum group-containing catalyst can be platinum group metal, platinum group metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. patent application Ser. No. 10/017,229, filed Dec. 7, 2001, such as (COD)Pt(SiMeCl$_2$)$_2$, where COD is 1,5-cyclooctadiene and Me is methyl. These alkene-platinum-silyl complexes may be prepared, for example by mixing 0.015 mole (COD)PtCl2 with 0.045 mole COD and 0.0612 moles HMeSiCl2.

The appropriate amount of the catalyst will depend upon the particular catalyst used. The platinum catalyst should be present in an amount sufficient to provide at least 2 parts per million (ppm), alternatively 4 to 200 ppm of platinum based on total weight percent solids (all non-solvent ingredients) in the composition. Typically, the platinum is present in an amount sufficient to provide 4 to 150 weight ppm of platinum on the same basis. The catalyst may be added as a single species or as a mixture of two or more different species.

D) The Second Polyoxyalkylene

The silicone organic elastomer contains pendant, non-crosslinking polyoxyalkylene groups. These groups are formed on the silicone organic elastomer via a hydrosilylation reaction by the addition of component D) a second polyoxyalkylene having the average formula $$R^3O—[(C_2H_4O)_{c'}(C_3H_6O)_{d'}(C_4H_8O)_{e'}]R^4$$

where $R^3$ is a monovalent unsaturated aliphatic hydrocarbon group containing 2 to 12 carbon atoms, c' is greater than 4, d' and e' may vary from 0 to 100, $R^4$ is hydrogen, an acyl group, or a monovalent hydrocarbon group containing 1 to 8 carbons, The unsaturated aliphatic hydrocarbon group in D can be an alkenyl or alkynyl group. Representative, non-limiting examples of the alkenyl groups are shown by the following structures; $H_2C=CH—$, $H_2C=CHCH_2—$, $H_2C=C(CH_3)CH_2—$, $H_2C=CHCH_2CH_2—$, $H_2C=CHCH_2CH_2CH_2—$, and $H_2C=CHCH_2CH_2CH_2CH_2—$. Representative, non-limiting examples of alkynyl groups are shown by the following structures; $HC≡C—$, $HC≡CCH_2—$, $HC≡CC(CH_3)—$, $HC≡CC(CH_3)_2—$, $HC≡CC(CH_3)_2CH_2—$.

Representative, non-limiting examples of polyoxyalkylenes, useful as component D) include;
$H_2C=CHCH_2O(C_2H_4O)_{c'}H$
$H_2C=CHCH_2O(C_2H_4O)_{c'}CH_3$
$H_2C=CHCH_2O(C_2H_4O)_{c'}C(O)CH_3$
$H_2C=CHCH_2O(C_2H_4O)_{c'}(C_3H_6O)_{d'}H$
$H_2C=CHCH_2O(C_2H_4O)_{c'}(C_3H_6O)_{d'}CH_3$
$H_2C=CHCH_2O(C_2H_4O)_{c'}C(O)CH_3$
$H_2C=C(CH_3)CH_2O(C_2H_4O)_{c'}H$
$H_2C=CC(CH_3)_2O(C_2H_4O)_{c'}H$
$H_2C=C(CH_3)CH_2O(C_2H_4O)_{c'}CH_3$
$H_2C=C(CH_3)CH_2O(C_2H_4O)_{c'}C(O)CH_3$
$H_2C=C(CH_3)CH_2O(C_2H_4O)_{c'}(C_3H_6O)_{d'}H$
$H_2C=C(CH_3)CH_2O(C_2H_4O)_{c'}(C_3H_6O)_{d'}CH_3$
$H_2C=C(CH_3)CH_2O(C_2H_4O)_{c'}C(O)CH_3$
$HC≡CCH_2O(C_2H_4O)_{c'}H$
$HC≡CCH_2O(C_2H_4O)_{c'}CH_3$
$HC≡CCH_2O(C_2H_4O)_{c'}C(O)CH_3$
$HC≡CCH_2O(C_2H_4O)_{c'}(C_3H_6O)_{d'}H$
$HC≡CCH_2O(C_2H_4O)_{c'}(C_3H_6O)_{d'}CH_3$
$HC≡CCH_2O(C_2H_4O)_{c'}C(O)CH_3$
where c' and d' are as defined above.

The polyether may also be selected from those as described in U.S. Pat. No. 6,987,157, which is herein incorporated by reference for its teaching of polyethers.

Component D may be added to the silicone organic elastomer either during formation (i.e. simultaneously reacting components A), B), C) and D), in a first reaction (for example reacting a partial quantity of SiH groups of component A) with C) and D), followed by further reaction with B) or subsequently added to a formed silicone organic elastomer having SiH content (for example, from unreacted SiH units present on the silicone organic elastomer).

The amount of components A, B, and D used in the hydrosilylation reaction may vary, providing the molar quantity of the total aliphatic unsaturated groups present in the reaction from components B) and D) is such that the molar ratio of the SiH units of component A) to the aliphatic unsaturated groups of components B) and D) ranges from 10/1 to 1/10. However, typically the molar ratio of the unsaturated aliphatic hydrocarbon groups in B) and D) to the SiH units in A) is greater than 1 to ensure complete consumption of SiH.

The amounts and structures of B) and D) used in the hydrosilylation may also vary. However, the amounts used and structures of B) and D) are such so as to provide a silicone organic elastomer having an ethylene oxide content of 2 to 25 weight percent, alternatively 3 to 20 weight percent, or alternatively 4 to 18 weight percent. As used herein, ethylene oxide content refers to the average amount of "EO" groups (that is $—CH_2CH_2O—$) present on the silicone organic elastomer structure.

In one embodiment, the silicone organic elastomer is crosslinked with a polyoxypropylene chain and the silicone organic elastomer further contains pendant polyoxyethylene units. In this embodiment, component B is selected to contain only propylene oxide as the polyoxyalkylene groups and component D contains only ethylene oxide as the polyoxyalkylene groups. Thus, in this embodiment, component B has the formula $R^3O—[(C_3H_6O)_{d'}]—R^3$, where $R^3$ is the same as defined above, and d' is greater than 0, alternatively d' may vary from 4 to 50, alternatively d' may vary from 10 to 30. Sufficient amounts of component B are used to provide the silicone elastomer with a propylene oxide content of 5 to 50 weight percent. In this embodiment, component B has the formula $R^3O—[(C_2H_4O)_{c'}]—R^4$ where $R^3$ and $R^4$ are the same as defined above, and c' is greater than 4, alternatively c' is greater than 4, or may vary from 4 to 50, alternatively c' may vary from 10 to 30. Sufficient amounts of component D are used to provide the silicone elastomer with a ethylene oxide content of 2 to 25 weight percent.

The order of addition of components A), B), C) and D) may vary. However, in one embodiment, the reaction to prepare the silicone elastomer proceeds in two steps. The first reacts components A), C), and D) to form an organohydrogensiloxane polyoxyethylene copolymer, the second reacts the organohydrogensiloxane polyoxyethylene copolymer with component B) and additional quantities of C).

(ii) The Carrier Fluid

The silicone organic elastomers (i) are contained in a carrier fluid (ii) to provide the silicone-organic gel compositions. Typically, the carrier fluid is the solvent used for conducting the hydrosilylation reaction to form the silicone organic elastomer. Suitable carrier fluids include, organic liquids (oils and solvents), silicones and mixtures of these.

Typically, the carrier fluid is an organic liquid. Organic liquids includes those considered oils or solvents. The organic liquids are exemplified by, but not limited to, aromatic hydrocarbons, aliphatic hydrocarbons, alcohols having more than 6 carbon atoms, aldehydes, ketones, amines, esters, ethers, glycols, glycol ethers, alkyl halides and aromatic halides. Hydrocarbons include, isododecane, isohexadecane, Isopar L (C11-C13), Isopar H (C11-C12), hydrogentated polydecene. Ethers and esters include, isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME). octyldodecyl neopentanoate, diisobutyl adipate, diisopropyl adipate, propylene glycol dicaprylate/dicaprate, and octyl palmitate. Additional organic carrier fluids suitable as a stand alone compound or as an ingredient to the carrier fluid include fats, oils, fatty acids, and fatty alcohols.

The carrier fluid may also be a low viscosity organopolysiloxane or a volatile methyl siloxane or a volatile ethyl siloxane or a volatile methyl ethyl siloxane having a viscosity at 25° C. in the range of 1 to 1,000 mm²/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy}trisiloxane, hexamethyl-3,3, bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes, and any mixtures thereof.

The amount of i) silicone organic elastomer and ii) carrier fluid is such that the composition contains 2-95 weight percent,
alternatively 5 to 95 weight percent
alternatively 10 to 90 weight percent of i) the silicone organic elastomer, and
5-98 weight percent,
alternatively 95 to 5 weight percent
alternatively 90 to 10 weight percent of ii) the carrier fluid, providing the sum of components i) and ii), and any other ingredients or components present in the composition, sum to 100 weight percent.

The silicone organic elastomer gels, as described above, are combined with water (or any aqueous solution) or a hydrophilic solvent to form paste compositions. Typically, the gels and water may be combined with simple mixing techniques. The amount of water or hydrophilic solvent added to the silicone organic elastomer gel may vary from 1 to 600 part water or hydrophilic solvent for every 100 parts of the silicone organic elastomer gel.

In one embodiment, the resulting paste composition is a water in oil emulsion.

Alternatively, a hydrophilic solvent may be used to create an anhydrous paste. For the purpose of illustration, hydrophilic solvents include lower molecular weight alcohols and glycols such as methanol, ethanol, propanol, isopropanol, butanol; glycols include propylene glycols, dipropylene glycols.

The Personal or Health Care Active

A personal or health care active may be added to the present compositions. As used herein, a "personal care active" means any compound or mixtures of compounds that are known in the art as additives in the personal care formulations that are typically added for the purpose of treating hair or skin to provide a cosmetic and/or aesthetic benefit. A "healthcare active" means any compound or mixtures of compounds that are known in the art to provide a pharmaceutical or medical benefit. Thus, "healthcare active" include materials consider as an active ingredient or active drug ingredient as generally used and defined by the United States Department of Health & Human Services Food and Drug Administration, contained in Title 21, Chapter I, of the Code of Federal Regulations, Parts 200-299 and Parts 300-499.

The amount of personal or healthcare active present in the silicone paste composition may vary, but typically range as follows;

0.02 to 50 wt %, alternatively 1 to 25 wt %, or alternatively 1 to 10 wt %, based on the total amount by weight of silicone paste composition. For extremely potent drugs, levels as low as 1 ppm may be used.

The personal or healthcare active may be added to the silicone organic paste composition either during the making of the silicone organic elastomer (pre-load method), or added after the formation of the silicone organic elastomer gel (post load method). Typically, if the personal or healthcare active is hydrophobic, it is added with the carrier fluid. If the personal or healthcare active is hydrophilic, it is added with the addition of water or hydrophilic solvent in the preparation of the silicone paste.

Useful active ingredients for use in the present compositions include vitamins and its derivatives, including "provitamins". Vitamins useful herein include, but are not limited to, Vitamin $A_1$, retinol, $C_2$-$C_{18}$ esters of retinol, vitamin E, tocopherol, esters of vitamin E, and mixtures thereof. Retinol includes trans-retinol, 1,3-cis-retinol, 11-cis-retinol, 9-cis-retinol, and 3,4-didehydro-retinol, Vitamin C and its derivatives, Vitamin $B_1$, Vitamin $B_2$, Pro Vitamin B5, panthenol, Vitamin $B_6$, Vitamin $B_{12}$, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate.

RETINOL, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Some examples of commercially available products suitable for use herein are Vitamin A Acetate and Vitamin C, both products of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

The active can be a protein, such as an enzyme. The internal inclusion of enzymes in these compositions have advantages to prevent enzymes from deactivating and maintain bioactive effects of enzymes for longer time. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Said protease include, but are not limited to, trypsin, chymotrypsin, pepsin, pancreatin and other mammalian enzymes; papain, bromelain and other botanical enzymes; subtilisin, epidermin, nisin, naringinase(L-rhammnosidase) urokinase and other bacterial enzymes. Said lipase include, but are not limited to, triacyl-glycerol lipases, monoacyl-glycerol lipases, lipoprotein lipases, e.g. steapsin, erepsin, pepsin, other mammalian, botanical, bacterial lipases and purified ones. Natural papain is preferred as said enzyme. Further, stimulating hormones, e.g. insulin, can be used together with these enzymes to boost the effectiveness of them.

The active may also be a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or sulfur containing compounds, as well as essential oils of natural or synthetic origin. Many of these perfume ingredients are described in detail in standard textbook references such as *Perfume and Flavour Chemicals,* 1969, S. Arctander, Montclair, N.J.

Fragrances may be exemplified by, but not limited to, perfume ketones and perfume aldehydes. Illustrative of the perfume ketones are buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl- Dihydrojasmonate, Menthone, Carvone, Camphor, Fenchone, Alpha-Ionone, Beta-Ionone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone,
Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbornane, 6,7-Dihydro-1,1,2,3,3-Pentamethyl-4(5H)-Indanone, 4-Damascol, Dulcinyl or Cassione, Gelsone, Hexylon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran.

More preferably, the perfume ketones are selected for its odor character from Alpha Damascone, Delta Damascone, Iso Damascone, Carvone, Gamma-Methyl-Ionone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl) propanal, dihydrocinnamic aldehyde, 1-methyl-4-(4-methyl-3-pentenyl)-3-cyclohexene-1-carbox aldehyde, 5 or 6 methoxy 10 hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, paratolylacetaldehyde; 4-methylphenylacetaldehyde, 2-methyl-4-(2,6-trimethyl-1-cyclohexen-1-yl)-2-butena I, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

More preferred aldehydes are selected for their odor character from 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P.T. Bucinal, lyral, cymal, methyl nonyl acetaldehyde, hexanal, trans-2-hexenal, and mixture thereof.

In the above list of perfume ingredients, some are commercial names conventionally known to one skilled in the art, and also includes isomers. Such isomers are also suitable for use in the present invention.

The active may also be one or more plant extract. Examples of these components are as follows: Ashitaba extract, avocado extract, hydrangea extract, Althea extract, Arnica extract, aloe extract, apricot extract, apricot kernel extract, *Ginkgo Biloba* extract, fennel extract, turmeric[*Curcuma*] extract, oolong tea extract, rose fruit extract, Echinacea extract, Scutellaria root extract, Phellodendro bark extract, Japanese Coptis extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, Artemisia extract, Glycyrrhiza extract, hibiscustea extract, Pyracantha Fortuneana Fruit extract, Kiwi extract, Cinchona extract, cucumber extract, guanocine, Gardenia extract, Sasa Albo-marginata extract, Sophora root extract, Walnut extract, Grapefruit extract, Clematis extract, Chlorella extract, mulberry extract, Gentiana extract, black tea extract, yeast extract, burdock extract, rice bran ferment extract, rice germ oil, comfrey extract, collagen, cowberry extract, Gardenia extract, Asiasarum Root extract, Family of Bupleurum extract, umbilical cord extract, Salvia extract, Saponaria extract, Bamboo extract, Crataegus fruit extract, Zanthoxylum fruit extract, shiitake extract, Rehmannia root extract, gromwell extract, *Perilla* extract, linden extract, Filipendula extract, peony extract, Calamus Root extract, white birch extract, Horsetail extract, Hedera Helix(Ivy) extract, hawthorn extract, *Sambucus nigra* extract, Achillea millefolium extract, *Mentha piperita* extract, sage extract, mallow extract, Cnidium officinale Root extract, Japanese green gentian extract, soybean extract, jujube extract, thyme extract, tea extract, clove extract, Gramineae *imperata* cyrillo extract, *Citrus unshiu* peel extract Japanese Angellica Root extract, Calendula extract, Peach Kernel extract, Bitter orange peel extract, Houttuyna cordata extract, tomato extract, natto extract, Ginseng extract, Green tea extract (camelliea sinesis), garlic extract, wild rose extract, hibiscus extract, Ophiopogon tuber extarct, Nelumbo nucifera extract, parsley extract, honey, hamamelis extract, *Parietaria* extract, Isodonis herba extract, bisabolol extract, Loquat extract, coltsfoot extract, butterbur extract, Porid cocos wolf extract, extract of butcher's broom, grape extract, propolis extract, *luffa* extract, safflower extract, peppermint extract, linden tree extract, Paeonia extract, hop extract, pine tree extract, horse chestnut extract, Mizu-bashou [Lysichiton camtschatcese] extract, Mukurossi peel extract, Melissa extract, peach extract, cornflower extract, eucalyptus extract, saxifrage extract, citron extract, *coix* extract, mugwort extract, lavender extract, apple extract, lettuce extract, lemon extract, Chinese milk vetch extract, rose extract, rosemary extract, Roman Chamomile extract, and royal jelly extract.

In one embodiment, the personal care active is a sunscreen agent. The sunscreen agent can be selected from any sunscreen agent known in the art to protect skin from the harmful effects of exposure to sunlight. The sunscreen compound is typically chosen from an organic compound, an inorganic compound, or mixtures thereof that absorbs ultraviolet (UV) light. Thus, representative non limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)] Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoylmethane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxybenzophenone-1 Copolymer.

The sunscreen agent can be a single one or combination of more than one. Alternatively, the sunscreen agent is a cinnamate based organic compound, or alternatively, the sunscreen agent is octyl methoxycinnamate, such as Uvinul® MC 80 an ester of para-methoxycinnamic acid and 2-ethylhexanol.

Representative, non limiting examples of healthcare actives useful in the present compositions are listed as follows.

Antiparasite Agents:

The biologically active substance contained in a composition of the present invention in a therapeutically effective amount may be an antiparasite agent, such as, but not limited to, hexachlorobenzene, carbamate, naturally occurring pyrethroids, permethrin, allethrin, malathion, piperonyl butoxide or mixtures of these drugs.

Antimicrobial Agents:

Antimicrobial agents, also referred to as germicidal agents, which may be used in compositions of the present invention include phenols, including cresols and resorcinols. Antibacterial compositions according to the present invention may be used to treat infections of the skin. An example of a very common skin infection is acne, which involve infestation of the sebaceous gland with *p. acnes*, as well as *Staphylococus aurus* or *Pseudomonas*. Various antibacterial agents have been utilized to treat acne, however, their efficacy is limited due to their low penetration into the hydrophobic environment of the sebaceous gland. The composition of the present invention, being hydrophobic by nature would facilitate an enhanced rate of penetration. Examples of useful antiacne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate and cholate.

Another example is parachlorometaxylenol, which is an antimicrobial agent and is suitable for use in the compositions described in the present invention.

Phenols, in concentrations of about 0.2, 1.0, and 1.3 percent by weight are bacteriostatic, bactericidal, and fungicidal, respectively. Several phenol derivatives are more potent than phenol itself, and the most important among these are the halogenated phenols and bis-phenols, the alkyl-substituted phenols and the resorcinols.

Hydrophobic antibacterials useful in the present invention include triclosan, triclocarbon, eucalyptol, menthol, methylsalicylate, thymol, and mixtures thereof. Preferred are triclosan and triclocarbon.

Antifungal Agents:

Fungal infections are another object of treatment using the compositions of the present invention. Superficial fungal infection of the skin is one of the commonest skin disease seen in general practice. Dermatophytosis is probably the most common superficial fungal infection of the skin. It is caused by a group of fungi, which are capable of metabolizing the keratin of human epidermis, nails or hair. There are 3 genera of dermatophytes causing dermatophytosis i.e., microsporum, *trichophyton* and *epidermophyton*.

Candidiasis is an infection caused by the yeast like fungus *Candida albicans* or occasionally other species of *Candida*. Clinical syndromes of candidiasis include (a) oral candidiasis (oral thrush); (b) candidiasis of the skin and genital mucous membrane; and (c) *candida paronychia*, which inflicts the nail.

The composition of the present invention can contain an antifungal drug, which is active against dermatophytes and candida. The drug may include azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and any combination thereof at a therapeutically effective concentration. U.S. Pat. No. 4,352,808 discloses 3-aralkyloxy-2,3-dihydro-2-(1H-imidazolylmethyl)benzo[b]thiophene compounds having antifungal and antibacterial activity.

Steroidal Antiinflammatory Agents:

Suitable steroidal antiinflammatory agents usable in the composition of the present invention may include, although are not limited to, corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amc, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and mixtures thereof may be used. The preferred steroidal antiinflammatory for use in the present invention is hydrocortisone.

Psoriasis is a very common chronic inflammatory skin disease, which may be the target of treatment using a composition of the present invention. Psoriasis is marked by periodic flare-ups of sharply defined red patches covered by a silvery, flaky surface.

Corticosteroid ointments, greasy preparations containing small amount of water, are commonly used for treating psoriasis. Their main disadvantage is in their stickiness, which remains for long time after treatment is over. Examples of other inflammatory diseases or disorders, which can be treated by the composition of the present invention, wherein the drug is a steroid are: seborrheic dermatitis of the face and trunk, seborrheic blepharitis, contact dermatitis, stasis dermatitis (gravitational eczema; varicose eczema), exfoliative dermatitis (erythroderma), lichen simplex chronicus, pemphigus, conjuctivitis and uveitis.

Topical antihistaminic preparations currently available include 1 percent and 2 percent diphenhydramine (Benadryl® and Caladryl®), 5 percent doxepin (Zonalon®) cream, phrilamine maleate, chlorpheniramine and tripelennamine, phenothiazines, promethazine hydrochloride (Phenergan®) and dimethindene maleate. These drugs, as well as additional antihistamines can also be included in the composition of the present invention.

Additionally, so-called "natural" antiinflammatory agents are useful in context of the present invention. For example, candelilla wax, alpha bisabolol, aloe vera, Manjistha (extracted from plants in the genus *Rubia*, particularly *Rubia cordifolia*), and Guggal (extracted from plants in the genus *Commiphora*, particularly *Commiphora mukul*, may be used as an active ingredient in the composition of the present invention.

Non-Steroidal Antiinflammatory Drugs (NSAIDs):

Another embodiment of the present invention is administration of non-steroidal antiinflammatory drugs (herein NSAIDs) using a composition of the present invention. NSAIDs have been used extensively in recent years for treatment of chronic rheumatic or arthritic conditions and for management of pain. The compounds are believed to bring relief by inhibiting biosynthesis of prostaglandins at affected joints or in other tissue areas. Salicylic acid, or aspirin, and ibuprofen are well-known examples of NSAIDs drugs. Examples of NSAIDs include the following categories: propionic to acid derivatives; acetic acid derivatives; fenamic acid derivatives; biphenylcarboxylic acid derivatives; and oxicams. All of these NSAIDs are fully described in the U.S. Pat. No. 4,985,459 to Sunshine et al. which is incorporated herein by reference. Examples of useful NSAIDs include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, mniroprofen, tioxaprofen, suprofen, alminoprofen, tiaprofenic acid, fluprofen and bucloxic acid.

Antioxidants/Radical Scavengers:

Suitable antioxidants/radical scavengers useful in context of the present invention include ascorbic acid (vitamin C) and its salts, tocopherol (vitamin E), and its derivatives such as tocopherol sorbate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used, as well as EDTA, BHT and the like.

Antibiotics:

Antibiotics which may be used in context of the composition of the present invention, include, but are not limited to, chloramphenicol, tetracyclines, synthetic and semi-synthesic penicillins, beta-lactames, quinolones, fluoroquinolnes, macrolide antibiotics, peptide antibiotics, cyclosporines, erytromycin and clinndamycin.

Topical Anesthetics:

Examples of topical anesthetic drugs useful in context of the composition of the present invention include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Retinoi:

Another preferred group of drugs useful in context of the composition of the present invention include retinol, all trans retinoic acid and derivatives, isomers and analogs thereof, collectively termed "retinoids". Compositions according to the present invention, which contain retinoids as the active ingredient can be used for the treatment of acne, seborrea, various dermatoses, inflammation of the skin, mucosal membranes, eye, vagina and the rectum, psoriasis and cancers, by application onto the affected area.

Anti-Viral Agents

Any anti-viral agent well-known to one of skill in the art can be used in the compositions and the methods of the invention. Non-limiting examples of anti-viral agents include proteins, polypeptides, peptides, fusion protein antibodies, nucleic acid molecules, organic molecules, inorganic molecules, and small molecules that inhibit or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, acyclovir prodrugs, famciclovir, gangcyclovir, vidarabine, idoxuridine, trifluridine, and ribavirin), n-docosanoll foscarnet, amantadine, rimantadine, saquinavir, indinavir, ritonavir, idoxuridine. alpha-interferons and other interferons, and AZT.

Anti-Cancer Drugs

Examples of anti-cancer agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin-2 (including recombinant interleukin 2, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epothilone A; epothilone B; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril;

merbarone; meterelin; methioninase; metoclopramide; MWF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl-lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vorozole; zanoterone; zeniplatin; zilascorb; and zinostatin stimalamer.

Other Drugs:

A broad range of analgesics may be utilized including, without limitation, morphine, codeine, heroine, methadone, thebaine, orpiarine, buprenorphine, morphinans, benzomorphans, acetaminophen, butorphanol, diflunisal, fenoprofen, fentanyl, fentanyl citrate, hydrocodone, aspirin, sodium salicylate, ibuprofen, oxymorphone, pentaxicine, naproxen, nalbuphine, mefenamic acid, meperidine and dihydroergotamine.

A typical narcotic antagonist is haloxone. Exemplary antitussive agents include, without limitation, diphenhydramine, guaifenesin, hydromorphone, ephedrine, phenylpropanolamine, theophylline, codeine, noscapine, levopropoxyphene, carbetapentane, chlorpehndianol and benzonatate.

Among the sedatives which may be utilized are, without limitation, chloral hydrate, butabarbital, alprazolam, amobarbital, chlordiazepoxide, diazepam, mephobarbital, secobarbital, diphenhydramine, ethinamate, flurazepam, halazepam, haloperidol, prochlorperazine, oxazepam, and talbutal.

Examples of cardiac drugs are, without limitation, quinidine, propranolol, nifedipine, procaine, dobutamine, digitoxin, phenyloin, sodium nitroprusside, nitroglycerin, verapamil HCl, digoxin, nicardipine HCl, and isosorbide dinitrate.

Antiemetics are illustrated by, without limitation, thiethylperazine, metoclopramide, cyclizine, meclizine, prochlorperazine, doxylamine succinate, promethazine, triflupromazine, and hydroxyzine.

A typical dopamine receptor agonist is bromocriptine mesylate. Exemplary amino acid, peptide and protein hormones include, without limitation, thyroxine, growth hormone (GH), interstitial cell stimulating hormone (ICSH), follicle-stimulating hormone (FSH), thyrotropic hormone (TSH), adrenocorticotropic hormone (ACTH), gonadotropin releasing hormone (GnRH) such as leuprolide acetate, vasopressin and their active degradation products Some products may have sufficiently high molecular weights that absorption through the stratum corneum or mucous membranes may be difficult. Therefore, the invention is applicable only to those hormones which have molecular weights and stereo configurations which will allow passage through the skin.

Female sex hormones which can be used include, without limitations, estradiol, diethylstilbestrol, conjugated estrogens, estrone, norethindrone, medroxyprogesterone, progesterone, and norgestrel.

Typical male sex hormones which may be utilized may be represented by, without limitation, testosterone, methyltestosterone, and fluoxymesterone.

In one embodiment, the healthcare active is selected from Nicotinamide, also known as niacinamide, lidocaine HCl, or clindamycin phosphate.

Process to Prepare Paste Compositions Containing the Silicone Organic Elastomer

The present disclosure further provides a process to prepare silicone paste compositions by;

I) reacting;

A) an organohydrogensiloxane comprising siloxy units of average

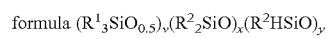

formula $(R^1{}_3SiO_{0.5})_v(R^2{}_2SiO)_x(R^2HSiO)_y$ wherein $R^1$ is hydrogen or $R^2$, $R^2$ is a monovalent hydrocarbyl, $v \geq 2$, $x \geq 0$, $y \geq 2$, B) a polyoxyalkylene having the average formula $R^3O-[(C_2H_4O)_c(C_3H_6O)_d(C_4H_8O)_e]-R^3$ wherein
$R^3$ is a monovalent unsaturated aliphatic hydrocarbon group containing 2 to 12 carbon atoms,
c is from 0 to 50, d is from 0 to 100, e is from 0 to 100, with a proviso the ratio of (d+e)/(c+d+e) is greater than 0.5, C) a hydrosilylation catalyst,
D) a polyoxyalkylene having the average formula $R^3O-[(C_2H_4O)_{c'}(C_3H_6O)_{d'}(C_4H_8O)_e]-R^4$ where $R^3$ is a monovalent unsaturated aliphatic hydrocarbon group containing 2 to 12 carbon atoms,
c' is greater than 4, d' and e may vary from 0 to 100,
$R^4$ is hydrogen, an acyl group, or a monovalent hydrocarbon group containing 1 to 8 carbons,
wherein the silicone organic elastomer has an ethylene oxide content of 2 to 25 weight percent,
in the presence of a hydrophobic carrier fluid to form a gel,
II) shearing the gel,
III) combining the sheared gel with additional quantities of the carrier fluid to form a gel paste composition,
IV) admixing water or a hydrophilic solvent to the gel paste composition.

The silicone organic elastomer gel compositions of the present invention may be considered as discrete crosslinked silicone organic elastomers dispersed in carrier fluids. The silicone organic elastomer gel compositions are also effective rheological thickeners for many organic and silicone fluids.

To make such silicone organic elastomer pastes, the aforementioned silicone organic elastomer gels of known initial elastomer content are sheared to obtain small particle size may optionally be further diluted to a final elastomer content. "Shearing", as used herein refers to any shear mixing process, such as obtained from homogenizing, sonalating, or any other mixing processes known in the art as shear mixing. The shear mixing of the silicone organic elastomer gel composition results in a composition having reduced particle size. The subsequent composition having reduced particle size is then further combined with additional quantities of ii) the carrier fluid. Typically, the amount of carrier fluid added to the gel to form the gel paste is sufficient to provide a gel paste composition containing 30 wt % of the silicone organic elastomer, alternatively 20 wt %, or alternatively 10 wt %. The carrier fluid may be any carrier fluid as described above. In one embodiment, the carrier fluid is an aliphatic hydrocarbon, such as those described above. In another embodiment, the carrier fluid is an organopolysiloxane having a viscosity at 25° C. in the range of 1 to 1,000 mm²/sec.

Step III involves combining the sheared gel with additional quantities of the carrier fluid. The technique for combining the ii) the carrier fluid with the silicone organic elastomer composition, and typically involves simple stirring or mixing. The resulting compositions may be considered as a paste, having a viscosity at least 50 Pa·s, alternatively at least 100 Pa·s, or alternatively at least 200 Pa·s, as measured on a Brookfield DVII+viscometer with Helipath attachment using spindle T-D (20.4 mm crossbar) at 2.5 rpm.

Step 1V involves admixing water or a hydrophilic solvent to the gel paste. Simple mixing techniques may be used to affect admixing in this step.

EXAMPLES

These examples are intended to illustrate the invention to one of ordinary skill in the art and should not be interpreted as limiting the scope of the invention set forth in the claims. All measurements and experiments were conducted at 23° C., unless indicated otherwise.

Materials

Organohydrogensiloxane 1=a dimethyl, methylhydrogen polysiloxane having an average formula of $(CH_3)_3SiO[(CH_3)_2SiO]_x[(CH_3)HSiO]_ySi(CH_3)_3$, where x~59.7 and y~7.3 and contains 0.146 wt. % H as Si—H.

Organohydrogensiloxane 2=a dimethyl, methylhydrogen polysiloxane having an average formula of $(CH_3)_3SiO[(CH_3)_2SiO]_x[(CH_3)HSiO]_ySi(CH_3)_3$, where x~91.0 and y~5.97 and contains 0.0828 wt. % H as Si—H.

Polyalkyloxylene 1=a monoallyl terminal poly(ethylene oxide) having an average structure of $CH_2=CHCH_2O(CH_2CH_2O)_{10.9}H$.

Polyalkyloxylene 2=a diallyl terminal poly(propylene oxide) having an average structure of $CH_2=CHCH_2O(CH_2CH(CH3)O)_{20.0}CH_2CH=CH_2$.

Polyalkyloxylene 3=a diallyl terminal poly(propylene oxide) having an average structure of $CH_2=CHCH_2O(CH_2CH(CH3)O)_{11.2}CH_2CH=CH_2$.

Pt Catalyst Solution 1=1.25 wt. % platinum as Karstedt's catalyst in dicaprylyl carbonate Pt Catalyst Solution 2=1.25 wt. % platinum as Karstedt's catalyst in isohexadecane Pt Catalyst Solution 3=1.26 wt. % platinum as Karstedt's catalyst in isodecyl neopentanoate Pt Catalyst Solution 4=1.40 wt % platinum as Karstedt's catalyst in a solution of dimethylvinylsiloxy-terminated dimethyl siloxane and tetramethyldivinyldisiloxane.

Pt Catalyst Solution 5=2.02 wt % platinum as Karstedt's catalyst in dicaprylyl carbonate.

Example 1

Preparation of Hydrophilic Elastomer Paste 1

First, 20.86 g (30.1 mmol Si—H) of Organohydrogensiloxane 1, 3.83 g (7.12 meq unsaturation) of Polyalkyloxylene 1, 134.27 g of dicaprylyl carbonate were placed in the reaction vessel along with a Teflon stirbar. The mixture was mixed and heated to 70° C. and 99 microliters of platinum catalyst solution was added to the reaction. The mixture was stirred at 70° C. for 25 minutes, at which time, 17.33 g (27.55 meq unsaturation) of Polyalkyloxylene 2, 44.50 g of dicaprylyl carbonate, and an additional 99 microliters of Pt Catalyst Solution 1 was added. The reaction vessel was held at 70° C. for 3 additional hours. Stirring was maintained until the mixture gelled. The result was a gel containing 19.1 wt. % of a hydrophilic silicone-organic elastomer in dicaprylyl carbonate. Using a blender, the gel was then sheared to form a paste and diluted with additional dicaprylyl carbonate to form a paste having 17.0 wt. % elastomer. Small amounts of a vinyl functional siloxane and triphenyl phosphine were added during the shear step to eliminate residual SiH and inhibit residual platinum. The resulting paste had a viscosity of 462,000 cP as measured using a Brookfield DVII Rheometer with Helipath adapter outfitted with a TD t-bar spindle rotating at 2.5 RPM.

Example 2

Preparation of Hydrophilic Elastomer Paste 2

First, 10.68 g (8.77 mmol Si—H) of Organohydrogensiloxane 2, 1.83 g (3.40 meq unsaturation) of Polyalkyloxylene 1, and 51.25 g of isohexadecane were placed in the reaction vessel along with a Teflon stirbar. The mixture mixed and heated to 70° C. and 42 microliters of Platinum catalyst solution 2 was added to the reaction. The mixture was stirred at 70° C. for 25 minutes, at which time, 2.51 g (6.70 meq unsaturation) of Polyalkyloxylene 3, 17.00 g of isohexadecane, and an additional 42 microliters of Pt Catalyst solution was added. The reaction vessel was held at 70° C. for 3 additional hours. Stirring was maintained until the mixture gelled. The result was a gel containing 18.1 wt. % of a hydrophilic silicone-organic elastomer in isohexadecane. Using a blender, the gel was then sheared to form a paste and a portion of the paste was diluted with additional isohexadecane in a Hauschild DAC 1500 FVZ Speedmixer to form a paste having 16.5 wt. % elastomer. Small amounts of a vinyl functional siloxane and triphenyl phosphine were added during the shear step to eliminate residual SiH and inhibit residual platinum. The resulting paste had a viscosity of 185,000 cP as measured using a Brookfield DVII Rheometer with Helipath adapter outfitted with a TD t-bar spindle rotating at 2.5 RPM.

Example 3

Preparation of a Water-in-Oil Gel Emulsion Containing a Sunscreen

To a Max 20 Speedmixer™ cup were added 0.15 g of octyl methoxycinnamate and 2.35 g Hydrophilic Elastomer Paste 1. The materials were mixed together for 15 seconds using a Hauschild DAC 1500 FVZ Speedmixer operated at 3540 RPM. 2.50 g of a 0.056 M MgSO4 solution was then added, and the cup was subjected to a total of ~2 minutes of mixing at 3540 RPM. The result was a thick white paste that shear thinned readily when applied to skin.

Example 4

Preparation of an Anhydrous Cosmetic Paste Containing a Propylene Glycol and a Sunscreen To a Max 20 Speedmixer™ cup were added 0.15 g of octyl methoxycinnamate and 2.85 g Hydrophilic Elastomer Paste 2. The materials were mixed together for 15 seconds using a Hauschild DAC 1500 FVZ Speedmixer operated at 3540 RPM. 2.01 g of a propylene glycol was then added, and the cup was subjected to a total of ~2 minutes of mixing at 3540 RPM. The resulting mixture was a thick translucent paste that shear thinned readily when applied to skin.

Example 5

Preparation and Active Release of a Water-in-Oil Paste Emulsion Containing Niacinamide Hydrophilic Elastomer Pastes 3 and 4 were prepared in a process similar to that described for Hydrophilic Elastomer Pastes 1 and 2. The gels were made with the compositions listed in Table 1. During the shear step, additional solvent and small amounts of a vinyl functional siloxane were added. The final paste for hydrophilic elastomer paste 3 had an elastomer content of 16.8% and a viscosity of 337,000 cP. The final paste for hydrophilic elastomer paste 4 had an elastomer content of 13.9% and a viscosity of 489,000 cP.

TABLE 1

|  | Hydrophilic Elastomer Paste 3 | Hydrophilic Elastomer Paste 4 |
| --- | --- | --- |
| organohydrogensiloxane 1 | 20.76 g |  |
| organohydrogensiloxane 2 |  | 28.03 g |
| polyalkyloxylene 1 | 3.81 g | 4.01 g |
| polyalkyloxylene 2 | 17.25 g | 11.97 g |
| Pt Catalyst solution 1 | 200.2 uL |  |
| Pt Catalyst solution 3 |  | 208.3 μL |
| dicapryl carbonate | 177.73 g |  |
| isodecyl neopentoate |  | 175.31 g |
| d-d-tocopherol | 0.88 g | 0.91 g |

Solutions containing niacinamide and deionized water were made at concentrations of 2%, 10% and 20% active. The niacinamide/water solution and the hydrophilic elastomer paste were added to a Max 10 Speedmixer™ cup according to the proportions listed in Table 2. The materials were mixed together for 60 seconds using a Hauschild DAC 1500 FVZ Speedmixer operated at the maximum setting. The resulting materials were white pastes.

TABLE 2

|  | 2% niacinamide solution | 10% niacinamide solution | 20% niacinamide solution | Hydrophilic Elastomer Paste 3 | Hydrophilic Elastomer Paste 4 |
| --- | --- | --- | --- | --- | --- |
| Sample A | 3.1 g |  |  | 3.1 g |  |
| Sample B |  | 3.1 g |  | 3.0 g |  |
| Sample C |  |  | 3.0 g | 3.0 g |  |
| Sample D | 3.0 g |  |  |  | 3.1 g |
| Sample E |  | 3.0 g |  |  | 3.0 g |
| Sample F |  |  | 3.0 g |  | 3.0 g |

Samples for drug release testing were prepared by drawing down a layer approximately 37 mil thick over an area of 1.9 cm² on a dialysis membrane. Each membrane was loaded into a modified Franz diffusion cell with a receptor medium of 0.9% saline. Temperature was maintained at 32° C. Samples of the receptor medium were taken at 1, 2, 3, 4, and 6 hours with full replacement of the receptor medium at each sampling interval. The receptor medium was analyzed for niacinamide content using an Ultra Performance Liquid Chromatography instrument manufactured by Waters Corporation. Data showing release of the active with time are shown in FIG. 1.

Example 6

Preparation and Active Release of a Water-in-Oil Paste Emulsion Containing Lidocaine HCl Hydrophilic Elastomer Pastes 5 and 6 were prepared in a process similar to that described for Hydrophilic Elastomer Pastes 1 and 2. Multiple batches of gels were made and combined. The gels were made with the compositions listed in Table 3. During the shear step, additional solvent and small amounts of triphenyl phosphine in a mixture of dodecamethylpentasiloxane and trimethyl-terminated dimethyl siloxane and a methyl vinyl cyclic siloxane were added. The final paste for hydrophilic elastomer paste 5 had an elastomer content of 17% and a viscosity of 488,500 cP. The final paste for hydrophilic elastomer paste 6 had an elastomer content of 13% and a viscosity of 407,900 cP.

TABLE 3

|  | Hydrophilic Elastomer gel for Paste 5 | Hydrophilic Elastomer gel for Paste 5 | Hydrophilic Elastomer gel for Paste 5 | Hydrophilic Elastomer gel for Paste 6 | Hydrophilic Elastomer gel for Paste 6 |
|---|---|---|---|---|---|
| Organohydrogensiloxane 1 | 23.76 g | 23.62 g | 23.62 g |  |  |
| Organohydrogensiloxane 2 |  |  |  | 32.19 g | 38.17 g |
| polyalkyloxylene 1 | 4.35 g | 4.33 g | 4.33 g | 4.59 g | 5.51 g |
| polyalkyloxylene 2 | 19.91 g | 19.62 g | 19.57 g | 13.78 g | 16.46 g |
| Pt Catalyst solution 4 | 0.345 g |  | 0.352 g | 0.464 g | 0.484 g |
| Pt Catalyst solution 5 |  | 111.0 uL |  |  |  |
| dicaprylyl carbonate | 201.87 g | 202.12 g | 202.12 g |  |  |
| isodecyl neopentanoate |  |  |  | 199.27 g | 239.26 g |

A solution containing lidocaine HCl and deionized water was made at a concentration of 10% active. The lidocaine HCl/water solution and the hydrophilic elastomer paste were added to a Max 10 Speedmixer™ cup according to the proportions listed in Table 4. The drug solution was initially added dropwise with shearing using a Hauschild AM501 Mixer. The remaining solution was then added to reach the totals in Table 4 and the materials were sheared for a total of 64 sec. The resulting materials were white pastes.

TABLE 4

|  | 10% lidocaine HCl solution | Hydrophilic Elastomer Paste 5 | Hydrophilic Elastomer Paste 6 |
|---|---|---|---|
| Sample G | 2.0 g | 2.0 g |  |
| Sample H | 2.0 g |  | 2.0 g |

Figure 2:
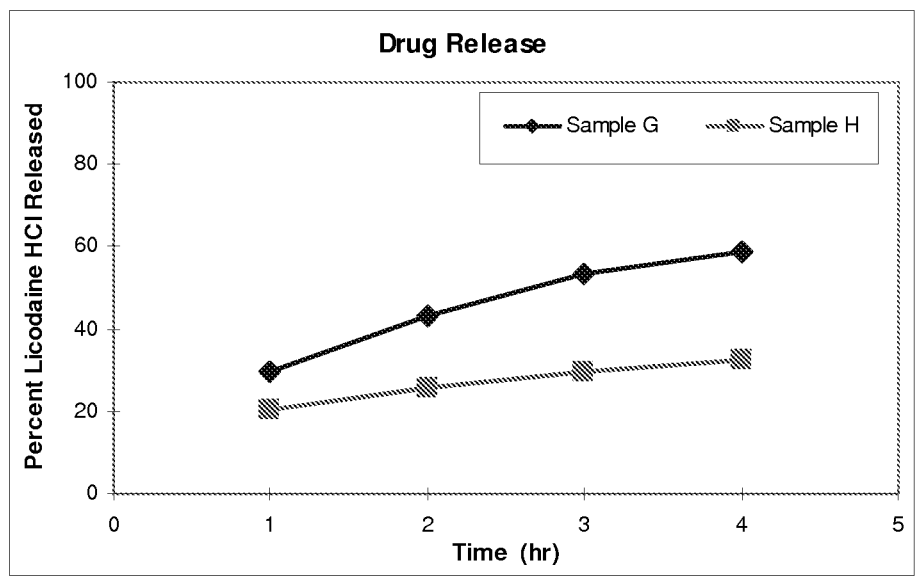

Samples for drug release testing were prepared by spreading approximately 43-54 mg over an area of 1.9 cm² on a polyether sulfone membrane. Each membrane was loaded into a modified Franz diffusion cell with a receptor medium of 0.9% phosphate buffered saline solution. Temperature was maintained at 32° C. Samples of the receptor medium were taken at 1, 2, 3, and 4 hours with full replacement of the receptor medium at each sampling interval. The receptor medium was analyzed for lidocaine HCl content using an Ultra Performance Liquid Chromatography instrument manufactured by Waters Corporation. Data showing release of the active with time are shown in FIG. 2.

Example 7

Preparation and Active Release of a Water-in-Oil Paste Emulsion Containing Clindamycin Phosphate Hydrophilic Elastomer Pastes 5 and 6 were prepared as described in Example 6. A solution containing clindamycin phosphate and deionized water was made at a concentration of 10% active. The clindamycin phosphate/water solution and the hydrophilic elastomer paste were added to a Max 10 Speedmixer™ cup according to the proportions listed in Table 5. The drug solution was initially added dropwise with shearing using a Hauschild AM501 Mixer. The remaining solution was then added to reach the totals in Table 5 and the materials were sheared for a total of 64 sec. The resulting materials were white pastes.

TABLE 5

|  | 10% clindamycin phosphate solution | Hydrophilic Elastomer Paste 5 | Hydrophilic Elastomer Paste 6 |
|---|---|---|---|
| Sample I | 2.0 g | 2.0 g |  |
| Sample J | 2.0 g |  | 2.0 g |

Figure 3:
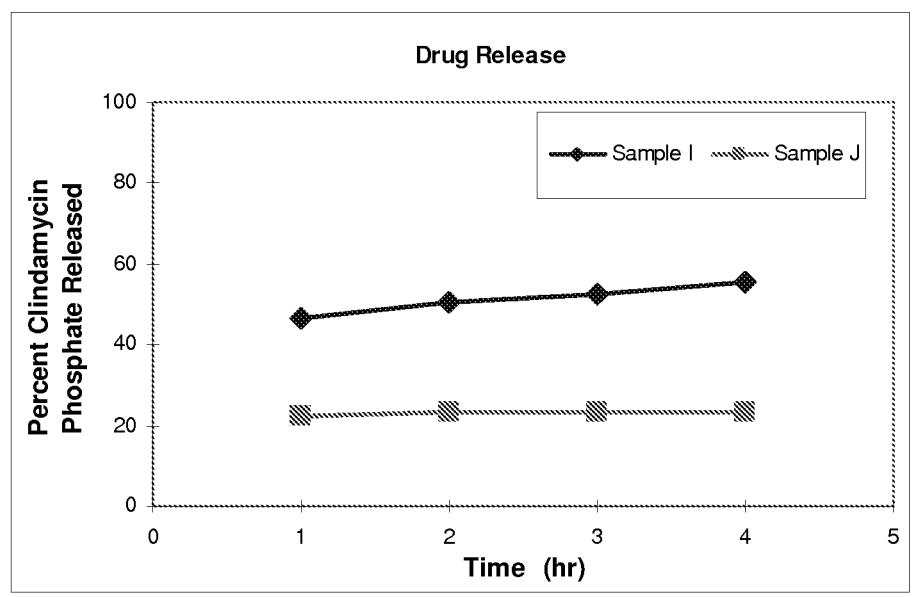

Samples for drug release testing were prepared by spreading approximately 45-53 mg over an area of 1.9 cm² on a polyether sulfone membrane. Each membrane was loaded into a modified Franz diffusion cell with a receptor medium of 0.9% phosphate buffered saline solution. Temperature was maintained at 32° C. Samples of the receptor medium were taken at 1, 2, 3, and 4 hours with full replacement of the receptor medium at each sampling interval. The receptor medium was analyzed for clindamycin phosphate content using an Ultra Performance Liquid Chromatography instrument manufactured by Waters Corporation. Data showing release of the active with time are shown in FIG. 3.

The invention claimed is:
1. A paste composition comprising:
a) 100 parts by weight of a silicone organic elastomer gel containing;
  i) 2-95 weight % of a silicone organic elastomer reaction product of;
    A) an organohydrogensiloxane comprising siloxy units of average formula $(R^1_3SiO_{0.5})_v(R^2_2SiO)_x(R^2HSiO)_y$
      wherein $R^1$ is hydrogen or $R^2$,
      $R^2$ is a monovalent hydrocarbyl,
      $v \geq 2$, $x \geq 0$, $y \geq 2$,
    B) a first polyoxyalkylene having the average formula $R^3O-[(C_2H_4O)_c(C_3H_6O)_d(C_4H_8O)_e]-R^3$ wherein
$R^3$ is a monovalent unsaturated aliphatic hydrocarbon group containing 2 to 12 carbon atoms,
c is from 0 to 50, d is from 0 to 100, e is from 0 to 100, with a proviso the ratio of (d+e)/(c+d+e) is greater than 0.5,
C) a hydrosilylation catalyst,
D) a second polyoxyalkylene having the average formula $$R^3O-[(C_2H_4O)_{c'}(C_3H_6O)_{d'}(C_4H_8O)_{e'}]-R^4$$

where $R^3$ is a monovalent unsaturated aliphatic hydrocarbon group containing 2 to 12 carbon atoms,
c' is greater than 4, d' and e' may vary from 0 to 100,
$R^4$ is hydrogen, an acyl group, or a monovalent hydrocarbon group containing 1 to 8 carbons,
wherein the silicone organic elastomer has an ethylene oxide content of 2 to 25 weight percent,
ii) 5-98 weight % of a hydrophobic carrier fluid,
b) 1 to 600 parts by weight of a hydrophilic solvent,
wherein the paste is anhydrous.

2. The paste composition of claim 1 further comprising a personal care or healthcare active.

3. The paste composition of claim 1 wherein the hydrophilic solvent is propylene glycol.

4. The paste composition of claim 1 wherein A) the organohydrogensiloxane is selected from an organohydrogensiloxane having the average formula $$(R^1{}_3SiO_{0.5})_v(R^2{}_2SiO)_x(R^2HSiO)_y(R^2SiO_{1.5})_z,$$

$$(R^1{}_3SiO_{0.5})_v(R^2{}_2SiO)_x(R^2HSiO)_y(SiO_2)_w,$$

$$(R^1{}_3SiO_{0.5})_v(R^2{}_2SiO)_x(R^2HSiO)_y(SiO_2)_w(R^2SiO_{1.5})_z$$

or any mixture thereof, where $R^1$ is hydrogen or $R^2$, $R^2$ is a monovalent hydrocarbyl, and $v \geq 2$, $w \geq 0$, $x \geq 0$, $y \geq 2$, and z is $\geq 0$.

5. The paste composition of claim 1 wherein the first polyoxyalkylene has an average formula selected from;

$$H_2C=CHCH_2O[C_3H_6O]_dCH_2CH=CH_2$$

$$H_2C=C(CH_3)CH_2O[C_3H_6O]_dCH_2C(CH_3)=CH_2$$

$$HC\equiv CCH_2O[C_3H_6]_dCH_2C\equiv CH, \text{ or}$$

$$HC\equiv CC(CH_3)_2O[C_3H_6O]_dC(CH_3)_2C\equiv CH$$

where d is greater than 1.

6. The paste composition of claim 1 wherein the second polyoxyalkylene has an average formula selected from;

$$H_2C=CHCH_2O[C_2H_4O]_{d'}H$$

$$H_2C=C(CH_3)CH_2O[C_2H_4O]_{c'}H$$

$$HC\equiv CCH_2O[C_2H_4O]_{c'}H, \text{ or}$$

$$HC\equiv CC(CH_3)_2O[C_2H_4O]_{c'}H$$

where c' is greater than 4.

7. The paste composition of claim 1 wherein the hydrophobic carrier fluid is dicaprylyl carbonate, isohexadecane, isodecyl neopentanoate, isododecane, or cyclopentasiloxane.

8. A process for preparing a paste composition comprising:
I) reacting;
A) an organohydrogensiloxane comprising siloxy units of average formula $(R^1{}_3SiO_{0.5})_v(R^2{}_2SiO)_x(R^2HSiO)_y$, wherein $R^1$ is hydrogen or $R^2$,
$R^2$ is a monovalent hydrocarbyl,
$v \geq 2$, $x \geq 0$, $y \geq 2$,
B) a polyoxyalkylene having the average formula $$R^3O-[(C_2H_4O)_c(C_3H_6O)_d(C_4H_8O)_e]-R^3$$

wherein
$R^3$ is a monovalent unsaturated aliphatic hydrocarbon group containing 2 to 12 carbon atoms,
c is from 0 to 50, d is from 0 to 100, e is from 0 to 100, with a proviso the ratio of (d+e)/(c+d+e) is greater than 0.5,
C) a hydrosilylation catalyst,
D) a polyoxyalkylene having the average formula $$R^3O-[(C_2H_4O)_{c'}(C_3H_6O)_{d'}(C_4H_8O)_{e'}]-R^4$$

where $R^3$ is a monovalent unsaturated aliphatic hydrocarbon group containing 2 to 12 carbon atoms,
c' is greater than 4, d' and e' may vary from 0 to 100,
$R^4$ is hydrogen, an acyl group, or a monovalent hydrocarbon group containing 1 to 8 carbons,
wherein the silicone organic elastomer has an ethylene oxide content of 2 to 25 weight percent,
in the presence of ii) a hydrophobic carrier fluid to form a gel,
II) shearing the gel,
III) combining the sheared gel with additional quantities of ii) the carrier fluid to form a gel paste composition,
IV) admixing a hydrophilic solvent to the gel paste composition.

9. The process of claim 8 wherein step I occurs in a first and second reaction, the first reaction of step I) reacts components A), C), and D) to form an organohydrogensiloxane polyoxyethylene copolymer, the second reaction of step I) reacts the organohydrogensiloxane polyoxyethylene copolymer with component B) and additional quantities of C).

10. The process of claim 9 further comprising the addition of a personal care or healthcare active.

11. The process of claim 10 wherein the active is a sunscreen agent.

12. The process of claim 11 wherein the sunscreen agent is octyl methoxycinnamate.

13. The process of claim 10 wherein the active is a hydrophilic drug.

14. The process of claim 13 wherein the hydrophilic drug is niacinamide, lidocaine HCl, or clindamycin phosphate.

15. The paste prepared according to the process of claim 8.

16. The paste prepared in claim 1 wherein the paste has a viscosity of at least 50 Pa·s at 23° C.

* * * * *